United States Patent [19]

Cipriani et al.

[11] 4,063,021

[45] Dec. 13, 1977

[54] METHOD FOR THE SYNTHESIS OF UREAS

[75] Inventors: Gioacchino Cipriani; Carlo Neri, both of San Donato Milanese (Milan), Italy

[73] Assignee: ANIC, S.p.A., Palermo, Italy

[21] Appl. No.: 639,441

[22] Filed: Dec. 10, 1975

[30] Foreign Application Priority Data

Dec. 10, 1974  Italy .................................. 30341/74

[51] Int. Cl.$^2$ .................. C07D 233/36; C07C 127/19
[52] U.S. Cl. ............................ 548/317; 260/239.3 A; 260/251 R; 260/553 A; 260/553 C; 260/553 R; 260/555 A
[58] Field of Search ............ 260/309.7, 553 R, 553 A, 260/553 C, 555 A, 239.3 A, 251 R

[56] References Cited

U.S. PATENT DOCUMENTS 2,276,696  3/1942  Olin .................................. 260/553 C
3,053,891  9/1962  Cook et al. ...................... 260/555 A
3,923,833  12/1975  Gruenman et al. ............... 260/309.7

OTHER PUBLICATIONS

Adams et al., Chem. Rev. 1965, vol. 65, pp. 573-574 relied upon.

*Primary Examiner*—Natalie Trousof
*Attorney, Agent, or Firm*—Ralph M. Watson

[57]  ABSTRACT

A method for the preparation of a group of variously substituted ureas is disclosed, these compounds being obtained by the pyrolytic decomposition of the alkali metal or alkaline earth metal carbamates corresponding to the expected ureas, the reaction taking place at a temperature of between 150° and 400° C under atmospherical pressures, and preferably under subatmospherical pressures, under which conditions the expected urea either sublimes or is distilled.

4 Claims, No Drawings

METHOD FOR THE SYNTHESIS OF UREAS

This invention relates to a method for the preparation of ureas having the formula:

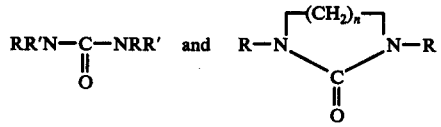

wherein N = 2, 3, 4 and R and R' are hydrogen, alkyl or aryl radicals, cycloalkyl, aralkyl or alkaryl radicals, either substituted or unsubstituted, either saturated or unsaturated, by pyrolysis of the corresponding carbamates having the formula:

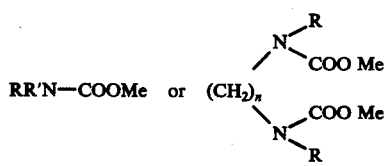

wherein Me is an alkali metal or an alkaline earth metal.

Such carbamates are prepared according to a method as disclosed in our copending patent application Ser. No. 639,442, filed Dec. 10, 1975.

The pyrolysis takes place according to the following reaction pattern:

at a temperature comprised between 150° and 400° C, at ambient pressure or, preferably, under subatmospherical pressures: under these conditions, urea either distils or sublimes.

EXAMPLE 1

20 grams of $C_6H_5NH$—COOLi are placed in a test-tube having a tail pipe, to be inserted into an electric oven and in which there is a vacuum of 20 millimeters of mercury (abs.press.).

The oven is heated to 300° C and on the walls of the test-tube 14 grams of biphenylurea sublime, the residue being constituted by 6 grams of $Li_2CO_3$.

EXAMPLE 2

20 grams of

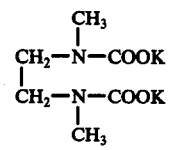

are treated as above at 350° C: 9 grams of $N_1,N^1$- dimethylethyleneurea, the residue is 11 grams of $K_2CO_3$.

What we claim is:

1. A method for the synthesis of a urea having the formula:

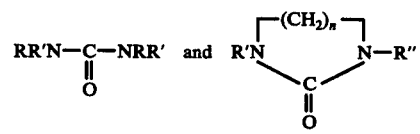

wherein $n$ is 2, 3, or 4, R is hydrogen, R' is phenyl and R'' is lower alkyl, which consists in pyrolyzing the corresponding carbamate having the formula:

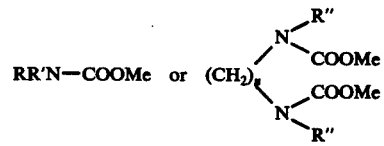

wherein $n$, R, R' and R'' have the meaning given above and Me is an alkali metal or an alkaline earth metal.

2. A method for the synthesis of a urea as claimed in claim 1 wherein the pyrolysis is carried out at a temperature in the range between 150° and 400° C.

3. A method of preparing biphenylurea which consists in pyrolyzing $C_6H_5$-NH-COOLi at a temperature of 300° C. at sub-atmospheric pressure.

4. A method of preparing $N_1$, $N^1$-dimethylethyleneurea which consists in pyrolyzing

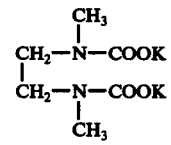

at a temperature of 350° C. and at sub-atmospheric pressure.

* * * * *